(12) United States Patent
Maurer et al.

(10) Patent No.: US 7,173,702 B2
(45) Date of Patent: Feb. 6, 2007

(54) SENSOR COMPRISING MULTI-WAVELENGTH LEDS

(75) Inventors: Scott M. Maurer, Haymarket, VA (US); Ryan C. Brewer, Bristow, VA (US); Larry D. Jackson, Manassas, VA (US); Kevin J. Kofler, Bristow, VA (US)

(73) Assignee: Lockheed Martin Corporation, Bethesda, MD (US)

( * ) Notice: Subject to any disclaimer, the term of this patent is extended or adjusted under 35 U.S.C. 154(b) by 314 days.

(21) Appl. No.: 10/891,573

(22) Filed: Jul. 15, 2004

(65) Prior Publication Data

US 2006/0014237 A1 Jan. 19, 2006

(51) Int. Cl.
*G01N 21/25* (2006.01)

(52) U.S. Cl. ..................... 356/417; 356/420

(58) Field of Classification Search .............. 356/417, 356/419, 420, 445
See application file for complete search history.

(56) References Cited

U.S. PATENT DOCUMENTS

| | | | |
|---|---|---|---|
| 4,552,458 A | * | 11/1985 | Lowne ..................... 356/446 |
| 4,651,010 A | * | 3/1987 | Javan ..................... 250/458.1 |
| 6,369,893 B1 | * | 4/2002 | Christel et al. ............. 356/417 |
| 6,940,598 B2 | * | 9/2005 | Christel et al. ............. 356/417 |
| 7,073,748 B2 | * | 7/2006 | Maurer et al. .............. 244/1 R |
| 2002/0109844 A1 | * | 8/2002 | Christel et al. ............. 356/417 |
| 2004/0106211 A1 | * | 6/2004 | Kauer et al. ................ 436/169 |
| 2004/0232052 A1 | * | 11/2004 | Call et al. .................... 209/143 |
| 2006/0011776 A1 | * | 1/2006 | Maurer et al. .............. 244/1 R |
| 2006/0014236 A1 | * | 1/2006 | Maurer et al. ................ 435/29 |
| 2006/0014300 A1 | * | 1/2006 | Maurer et al. .............. 436/518 |

* cited by examiner

*Primary Examiner*—Gregory J. Toatley, Jr.
*Assistant Examiner*—Roy M. Punnoose
(74) *Attorney, Agent, or Firm*—DeMont & Breyer, LLC

(57) ABSTRACT

The illustrative embodiment of the present invention is a system and a method for the detection and identification of biological agents. The system incorporates elements that enable it to obtain an air sample, extract particulates from the air sample onto a stationary-phase collection media, expose the particulates to electromagnetic radiation, and monitor for fluorescent emissions. In some embodiments, particulates are exposed to electromagnetic radiation using a plurality of LEDs, wherein some of the LEDs emit electromagnetic radiation at relatively shorter wavelengths and some other of the LEDs emit electromagnetic radiation at relatively longer wavelengths.

19 Claims, 4 Drawing Sheets

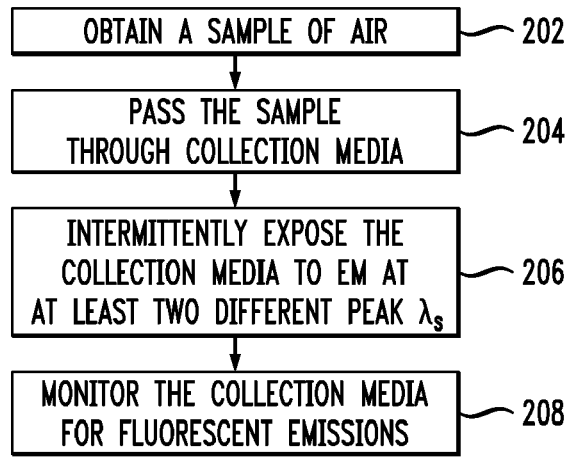
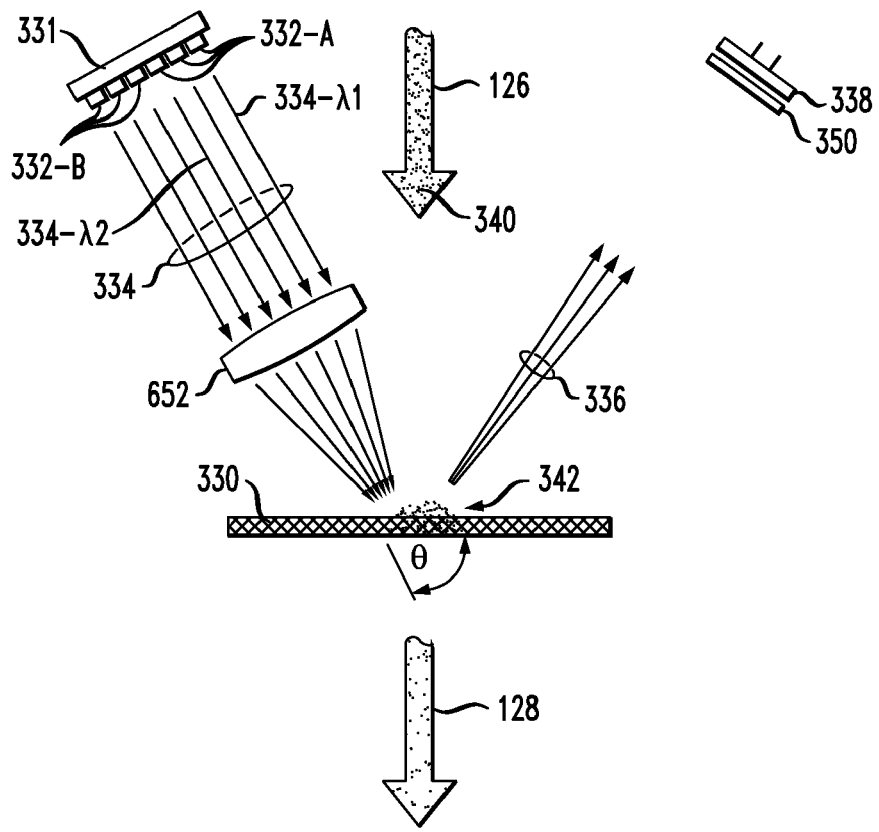

SENSOR COMPRISING MULTI-WAVELENGTH LEDS

STATEMENT OF RELATED CASES

This case is related to co-pending U.S. patent application Ser. Nos. 10/891,644, 10/891,805, 10/891,812 and 10/891,638, which were filed on even date herewith and are incorporated herein by reference.

BACKGROUND OF THE INVENTION

Biological warfare is the intentional use of microorganisms and toxins of microbial, plant or animal origin to produce diseases and/or death in humans, livestock and crops. To terrorists, biological warfare is attractive because bio-weapons have relatively low production cost, it is relatively easy to obtain a wide variety of disease-producing biological agents, bio-weapons are non-detectable by routine security systems, and bio-weapons are easily transportable.

Unlike relatively mature radiation- and chemical-detection technologies, early-warning technology for biological agents is in its infancy. Most known bio-detection systems are "flow-through," wherein individual particles that are contained in a flowing stream (e.g., air, etc.) are interrogated in an optical cell. Interrogation is typically performed using high-power lasers. The flowing stream, and hence the particles, have an extremely low residence time in the optical cell. As a consequence, the laser samples only a portion of the stream, must be relatively high power to provide an appropriate signal-to-noise ratio, and must be operating constantly to ensure detection.

Furthermore, some bio-detection systems use consumables, such as buffered saline solutions, antibodies, assay strips, reagent solutions, cleansing solution and antibodies. Most of these consumables have a specific shelf life, which creates a logistical burden. Furthermore, these consumables are typically unable to withstand demanding thermal requirements in theater. Also, many current bio-detection systems are large, heavy, and consume large amounts of power.

The drawbacks of prior-art bio-detection systems, as described above, significantly limit their usefulness in the field.

SUMMARY

The illustrative embodiment of the present invention is a sensing system and method for the detection and limited identification of biological agents. Unlike many prior-art bio-detection systems, the sensing system is small, light weight, requires little power to operate and uses few consumables. The system can be configured for use in either stationary or mobile applications.

The principle of operation for the sensing system is that many biological agents "fluoresce" when excited by radiation that has an appropriate wavelength, which is typically within or near the ultraviolet range. "Fluorescence" is the radiation that is emitted from a biological agent (or other substances) when it is excited as described above. What occurs at a molecular level is that the substance absorbs a photon of electromagnetic radiation, which causes an electron in the substance to move from a low energy state to a higher one. When the electron returns to a lower energy state, a photon is emitted. This photon is fluorescent radiation.

Since many types of biological agents fluoresce under ultraviolet light, the detection of fluorescent emissions from a sample that has been exposed to radiation having a wavelength in or near the ultraviolet range indicates that biological agents might be present. This is the detection function of the sensing system; some embodiments of the sensing system also provide an identification function as well.

Regarding identification, different biological agents contain different fluorescing organic substances (e.g., differing in amount or type). As a consequence, the peak intensity of the fluorescence emissions and/or characteristic fluorescent spectra for these different biological agents will be different. Furthermore, to the extent that different biological agents contain different fluorescing organic substances, the wavelength of the electromagnetic energy that is required to excite fluorescence will vary. Also, a given biological agent will exhibit a different fluorescence response (e.g., intensity, etc.) as a function of the wavelength of the excitation light. These attributes provide a basis for identification of biological agents.

Briefly, in a method in accordance with the illustrative embodiment:
  a an air sample is obtained;
  a particulates are extracted from the air sample;
  the particulates are exposed to electromagnetic radiation (typically in the ultraviolet to blue range of wavelengths) at at least two different peak wavelengths; and
  the particulates are monitored for fluorescent emissions.

To the extent that fluorescent emissions are detected and exceed a predetermined value, it is indicative that a biological attack might be in progress or might have occurred. Characteristics of the fluorescent emissions (e.g., wavelength, intensity, etc.) can be used to identify a biological agent that has been detected by the system.

A sensing system in accordance with the illustrative embodiment comprises an interrogation cell, which has:
  A stationary-phase collection media for extracting and retaining particulates, including biological agents, from an air sample.
  A source of electromagnetic radiation for exposing particulates that have been retained in the collection media. If the retained particulates include biological agents, they will fluoresce when exposed to electromagnetic radiation having an appropriate wavelength. Wavelengths within a range of about 250 to about 500 nanometers are appropriate for causing fluorescence in many biological agents. In the illustrative embodiment, the source of electromagnetic radiation is two or more light emitting diodes (LEDs), wherein at least one of the LEDs has a different peak emission wavelength than at least one other LED.
  A detector, such as a photodetector, for monitoring fluorescent emissions. The detector must be sensitive to the wavelengths of radiation at which biological agents fluoresce. The peak wavelength(s) of fluorescent emissions from biological agents of interest is typically in the range of about 300 to about 600 nanometers.

In addition to the interrogation cell, the sensing system also includes control/data-acquisition/data-processing circuitry. This circuitry is capable of implementing the following functions, among others:
  Controlling the operation of the source of electromagnetic radiation, including an ability to intermittently activate the sources as a function of peak emission wavelength.

Controlling the operation of the detector including activating the detector and acquiring data from the detector.

Signal processing. A signal generated by the photodetector is processed to:
- detect: determine if a biological agent is present in the air sample;
- quantify: estimate the amount of biological agent present, if any;
- assess: determine if the amount of a biological agent present is indicative of a biological attack or otherwise poses a risk to the health of the local population, livestock, etc.; and
- identify: determine the identity of a biological agent that is detected.

As indicated above, in some embodiments, some of the LEDs emit electromagnetic radiation having a peak wavelength that is different from some other of the LEDs. For example, some of the LEDs emit radiation at relatively shorter wavelengths in the ultraviolet range (hereinafter "shorter-wavelength LEDs"), while other of the LEDs emit light at relatively longer wavelengths in the ultraviolet range, violet or blue wavelengths (hereinafter "longer-wavelength LEDs"). Compared to a system that uses a single frequency of excitation light, a system that uses multiple wavelengths of excitation light provides an enhanced ability to identify any biological agents that have been detected.

BRIEF DESCRIPTION OF THE DRAWINGS

FIG. 2 depicts a method for the detection of biological agents in accordance with the illustrative embodiment of the present invention.

FIG. 3 depicts an interrogation cell of the sensing system of FIG. 1.

DETAILED DESCRIPTION

The illustrative embodiment of the present invention is a sensing system and method for the detection and limited identification of biological agents. In some embodiments, the sensing system is very light and quite small, fitting in an enclosure that is about 1 inch×1 inch×2 inches. The system can be configured for use in either stationary or mobile applications.

Biological agents of interest here typically have a size that is in a range of hundreds of nanometers (e.g., for viruses, etc.) to a few microns (e.g., for bacteria, etc). Typical biological agents of interest include, for example, anthrax (1×2 micron), plague (0.5×1 micron), tularemia (0.5×1 micron), and small pox (200×250×250 nanometers). The illustrative embodiment of the present sensing system is capable of detecting particles in this size range. In some variations of the illustrative embodiment, the sensing system is configured to detect smaller biological agents, and in yet some additional variations, the sensing system is configured to detect larger biological agents.

Figure 1:
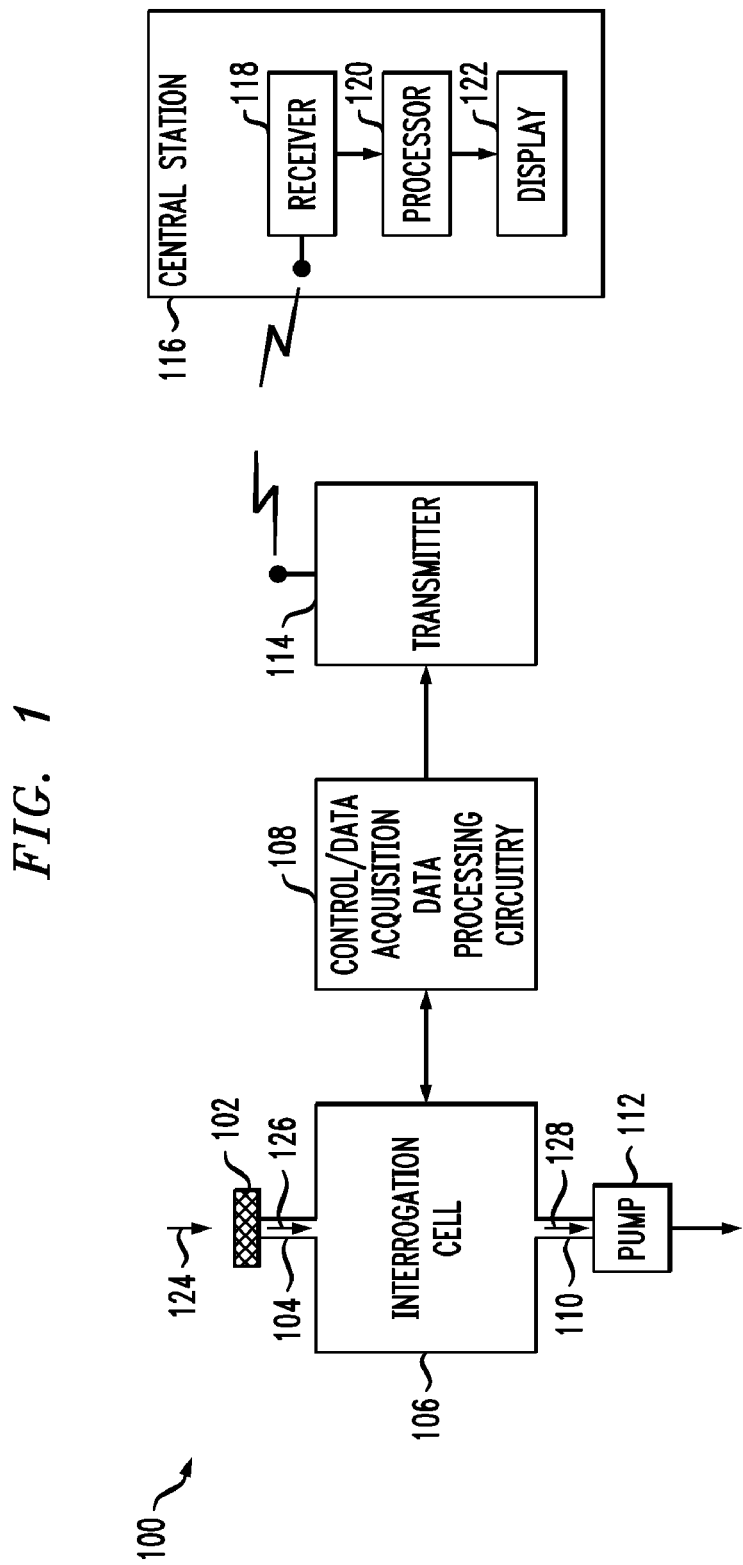
FIG. 1 depicts a sensing system for the detection of biological agents in accordance with the illustrative embodiment of the present invention.

FIG. 1 depicts sensing system 100 in accordance with the illustrative embodiment of the present invention. Sensing system 100 comprises interrogation cell 106, control/data acquisition/data processing circuitry 108, and central station 116, interrelated as shown.

A sample of air is obtained from the ambient environment for interrogation within interrogation cell 106. If sensing system 100 is stationary, then air is drawn through the sensing system by pump 112 or other similar device (e.g., a device that generates a suction flow, etc.). If the sensing system is moving (e.g., disposed on a vehicle, attached to a device that rotates the system, etc.), then pump 112 might not be necessary as a function of the speed at which sensing system 100 is moved.

In the illustrative embodiment, the sample of air, identified as flow 124 in FIG. 1, is filtered before it enters interrogation cell 106. In the illustrative embodiment, filtration is performed by filter 102, which is disposed upstream of cell inlet line 104.

Filter 102 prevents large particulate matter from entering interrogation cell 106. If large particulates were to enter interrogation cell 106, they might clog the interrogation cell, thereby shortening run time. In some embodiments, filter 102 filters particulate matter that is larger than about 50 microns. At this size, filter 102 will trap large dust particles, insects, and the like. Since, as described above, most biological agents of interest are much smaller than 50 microns, they will readily pass filter 102 and enter interrogation cell 106.

Filter elements suitable for use in the illustrative embodiment as filter 102 have a 50-micron pore structure and include, without limitation:

| glass micro-fiber | paper | anodized aluminum |
| Teflon ®-based materials | stainless steel | polymers/plastics. |

At least some of these filter elements are available from Donaldson Company of Minneapolis, Minn.; the other elements are available from any of a variety of commercial suppliers.

As an alternative to filter 102, a micro virtual impactor concentrator (micro-VIC®) can be used. The micro-VIC®, which is available from MesoSystems Technology, Inc. of Albuquerque, N. Mex., utilizes inertial effects to discharge and separate larger particulates from relatively smaller biological agents. Another alternative to a filter is a rotating-arm impactor.

Filtered flow 126 of air is conducted via cell inlet line 104 to interrogation cell 106. As described more fully later in this specification, particulates are removed from filtered flow 126 and interrogated in the interrogation cell. After passing through interrogation cell 106, substantially particulate-free flow 128 of air is expelled from sensing system 100 via cell outlet line 110.

The operation of interrogation cell 106 is controlled by control/data acquisition/data processing circuitry 108. Information that is obtained from the interrogation of the particulates is transmitted to station 116, which, in the illustrative embodiment, is remote from interrogation cell 106. In the illustrative embodiment, transmission is performed wirelessly via transmitter 114. The transmitted information is received by receiver 118, is processed as required in processor 120, and is displayed on display 122. In some alternative embodiments, control/data acquisition/data processing circuitry 108 is wired to station 116.

Having provided an overview of sensing system 100, description of the operation and structure of interrogation cell 106 is now provided. The description proceeds with reference to FIG. 2, which depicts method 200 for detection of biological agents, and FIG. 3, which depicts the structure of interrogation cell 106.

Method 200 includes the following operations:
- obtaining a sample of air (operation 202);
- passing the sample of air through a collection media, wherein the collection media is capable of retaining particulates that are contained in the sample of air (operation 204);
- intermittently exposing the retained particles to electromagnetic radiation at at least two different peak wavelengths (operation 206); and
- monitoring for fluorescent emissions (operation 208).

Operation 202 of method 200 recites "obtaining a sample of air." A purpose of operation 202 is to provide a sample of air for interrogation by interrogation cell 106.

Operation 204 of method 200 recites "passing the sample through collection media, wherein the collection media is capable of retaining particles contained in the sample." A purpose of operation 204 is to extract any biological agents that might be contained within the air sample (i.e., filtered air sample 126) so that they can be interrogated.

Referring now to FIG. 3, filtered air flow 126 is directed to stationary-phase collection media 330. The collection media comprises a stationary phase that is physically adapted to trap at least about 99 percent of particulates 340 that remain in filtered air flow 126 and have a size in the range of interest for biological agents (i.e., about 0.3–5 microns). Particulates that are retained by collection media 330 compose sample 342. Interrogation cell 106 can be provided with stationary-phase collection media 330 having a more definitive rating to the extent that it is intended to monitor a specific type of threat (i.e., a particular biological agent).

Stationary-phase collection media 330 suitable for use in conjunction with sensing system 100, as a function of the biological agents of interest, includes:
- HEPA/ULPA glass microfiber filtration media that is rated at >99.7% removal efficiency for particulates at 0.3 microns.
- PTFE/PFA/PFE (i.e., Teflon®-based) filtration media that is rated at >99% for particulates at 0.3 microns.
- Paper filtration media that is rated at >99% for particulates at 0.3 microns.
- Stainless Steel filtration media that is rated at >99% for particulates at 1 micron.
- Anodized Aluminum filtration media that is rated at >99% for particulates at 1 micron.
- Other types of filtration media such as plastics and other polymers that are rated at >99% for particulates at 0.3 microns.

As previously indicated, after passing through collection media 330, the now substantially particulate-free flow 128 of air is expelled to the ambient environment via cell outlet line 110.

In some embodiments, even those in which the sensing system 100 is mobile, an appropriately-valved pump is included in the system and used to reverse the flow of air through collection media 330. Reversing the flow of air removes at least some of the material (i.e., particulates 340) that has been retained by collection media 330. Reversing the flow in this manner might be necessary if the collection media becomes clogged. Alternatively, this technique can be used to establish a new interrogation baseline (e.g., for fluorescent emissions, etc.).

Operation 206 of method 200 recites "intermittently exposing the collection media to electromagnetic radiation at at least two different peak wavelengths." A purpose of this operation is to intermittently excite to fluorescence any biological agents that have been trapped by collection media 110. Using at least two different peak wavelengths enhances the ability of system 100 to identify, as opposed to simply detecting the presence of a biological agent. Since most biological agents of interest are excited by wavelengths between about 250 to 500 nanometers (i.e., ultraviolet to blue), the peak emission wavelength of the excitation sources should be within this range. LEDs emit radiation over a range of wavelengths. Typically, one wavelength will contain more energy than any other single wavelength. That one wavelength is the "peak emission wavelength."

With reference to FIG. 3, sensing system 100 includes LED array 331 comprising a plurality of LEDs; in particular, one or more LEDs 332-A and one or more LEDs 332-B. In the illustrative embodiment, the LEDs are the source of electromagnetic radiation. LEDs 332-A emit radiation 336 having a peak wavelength $\lambda 1$, which is different than the wavelength $\lambda 2$ of the radiation emitted by LEDs 332-B. LEDs 332-A emit electromagnetic radiation at different times than LEDs 332-B. The LEDs are controlled for intermittent operation as a function of emission wavelength via control/data acquisition/data processing circuitry. Further description of the use of multiple peak emission wavelengths for the identification of unknown biological agents is provided later in this specification.

Radiation 336 from the LEDs is focused, via lens 652, at sample 342. LED Array 331 can be positioned at any out-of-plane angle $\theta$ relative to collection media 330. The angle $\theta$ is typically in the range of 0 to 90 degrees, and more typically between 45 to 60 degrees.

The LEDs do not remain on continuously; rather, they are pulsed "on" and "off." In comparison with an "always-on" laser-based system, the use of an LED, especially in a pulsed mode, consumes far less power. For example, average power consumption for a pump-less system is expected to be about 100 mW at 5V. Sensing system 100 is adaptable for battery operation, as desired, at 6, 12 or 24 volts DC.

Operation 208 of method 200 recites "monitoring for fluorescent emissions." A purpose of this operation is to detect the presence of biological agents and, in some cases, to identify them. Interrogation cell 106 includes a photodetector for this purpose.

Referring now to FIG. 3, interrogation cell 106 includes at least one photodetector array 338, which comprises a plurality of photodetectors, for monitoring fluorescent emissions 336 from any biological agents that are present in sample 342 on collection media 330. In the illustrative embodiment, the photodetectors are photodiodes. Photodetector array 338 must be sensitive to at least the wavelengths of the fluorescent emissions from biological agents of interest. Most biological agents of interest fluoresce at wavelengths that are within the range of about 300 to about 600 nanometers. For example, tryptophan (an amino acid that is typically found in animal proteins or bacteria) has a peak emission at about 330 nanometers, NADH (usually associated with growth media and yeast grown products that are used for culturing organisms) has a peak at around 450 nanometers and flavins (again associated with growth media) have a peak at around 560 nanometers. As a consequence, photodetector array 338 should include photodetectors that are sensitive to wavelengths in this range.

Filter 350 is used in conjunction with the photodetectors to capture the desired wavelengths for each photodetector in photodetector array 338. Photodetector arrays 338 suitable for use in conjunction with this embodiment are available from Texas Advanced Optoelectronic Solutions (TAOS), Inc. of Plano, Tex. and others. One such suitable array, for example, is available as TAOS TCS230, which is an RGB photodiode array comprising an 8×8 staggered arrangement of RGB and clear photodiodes.

In some other embodiments, interrogation cell 106 incorporates multiple individual photodetectors, rather than a photodetector array.

Control/data acquisition/data processing circuitry 108 (FIG. 1) controls much of the operation of interrogation cell 106. In this context, this circuitry, which in some embodiments includes a processor and memory, is capable of:
  a driving LED(s) 332; and
  capable of intermittently pulsing LED(s) 332A and 332B as a function of peak emission wavelength; and
  enabling photodetector(s) 338.

Photodetector 338 generates a signal(s) in known fashion when it receives fluorescent emissions 336. The signal(s) contains information pertaining to the fluorescent emissions. For example, in some embodiments, the signal(s) is indicative of the wavelength(s) of the fluorescent emissions and the intensity of those emissions. This information can be used to develop a relative "particulate" (i.e., biological agent) count as a function of wavelength.

Control/data-acquisition/data-processing circuitry 108 receives the signal(s) from the photodetector (representative of the fluorescent emissions) and performs one or more of the following tasks:
  stores a representation of the signal; and/or
  partially processes the signal; and/or
  fully processes the signal; and/or
  transmits (in conjunction with transmitter 114), to central station 116:
    a representation of the signal; or
    a representation of the signal as well as data obtained from partially processing the signal; or
    a representation of the signal as well as data obtained from fully processing the signal; or
    only the information obtained from processing the signal.

In some embodiments, operation 208 (i.e., monitoring the collection media for fluorescent emissions) also includes the task(s) described above.

As indicated above, in some embodiments, at least some processing of the signal(s) from photodetector 338 is performed at central station 116. Doing so facilitates using additional, more powerful data-processing algorithms to analyze the information contained in the signals.

The information obtained from the signal(s) from photodetector 338 can be used to:
  detect biological agents;
  estimate the amount of biological agent detected;
  determine if the amount of biological agent present is indicative of a biological attack or otherwise poses a risk to the health of the local population, livestock, etc.;
  identify the biological agents that are detected.

If the information obtained from photodetector array 338 indicates the possibility of elevated levels of a biological agent (see, e.g., applicant's co-pending application, Dkt. No. 711-016, entitled "SYSTEM FOR THE DETECTION OF BIOLOGICAL AGENTS"), then an attempt is made to identify the biological agent.

It was previously disclosed that exposing sample 342 to more than one peak emission wavelength enhances the ability of sensing system 100 to identify a biological agent, once detected. In this context, identification includes "ruling-out" certain possibilities as to the identity of a compound. In other words, as used herein, "identification" can mean:
  positive identification of a detected biological agent;
  a narrowed list of possibilities as to the identity of a detected biological agent;
  a list of biological agents that are ruled out as candidates for the identity of a detected biological agent;
  a list of "possibles" and a list of "not possibles" as to the identity of a detected biological agent.

As to the peak emission wavelengths of LEDs 332-A and 332-B, in some embodiments, LEDs 332-A emit light at a peak wavelength that is less than about 300 nanometers while LEDs 332-B emit light at a peak wavelength that is greater than about 300 nanometers. In some other embodiments, LEDs 332-A emit light at a peak wavelength that is less than about 300 nanometers while LEDs 332-B emit light at a peak wavelength that is greater than about 350 nanometers. In yet some additional embodiments, LEDs 332-A emit light at a peak wavelength that is less than about 300 nanometers while LEDs 332-B emit light at a peak wavelength that is greater than about 400 nanometers. In some further embodiments, LEDs 332-A emit light at a peak wavelength that is less than about 350 nanometers while LEDs 332-B emit light at a peak wavelength that is greater than about 380 nanometers. In yet some further embodiments, LEDs 332-A emit light at a peak wavelength that is less than about 400 nanometers while LEDs 332-B emit light at a peak wavelength that is greater than about 400 nanometers.

Currently, an emission wavelength of 275 nanometers for an LED is a practical minimum. As LEDs are developed that are capable of lower emission wavelengths, those skilled in the art will be able to use them in conjunction with the illustrative embodiment of the present invention to improve the identification of unknown biological agents.

Figure 4:
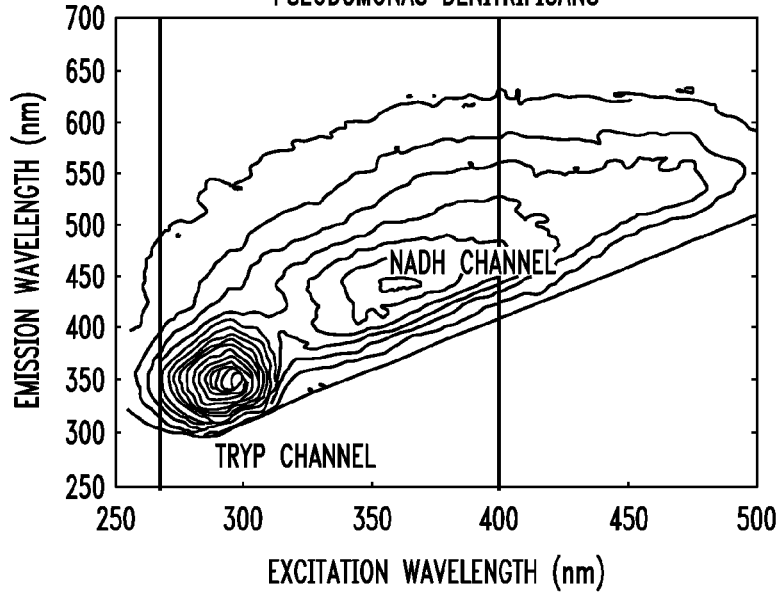
FIG. 4 depicts the total fluorescence spectrum of pseudomonas denitrificans, showing emission wavelength as a function of excitation wavelength.
Figure 5:
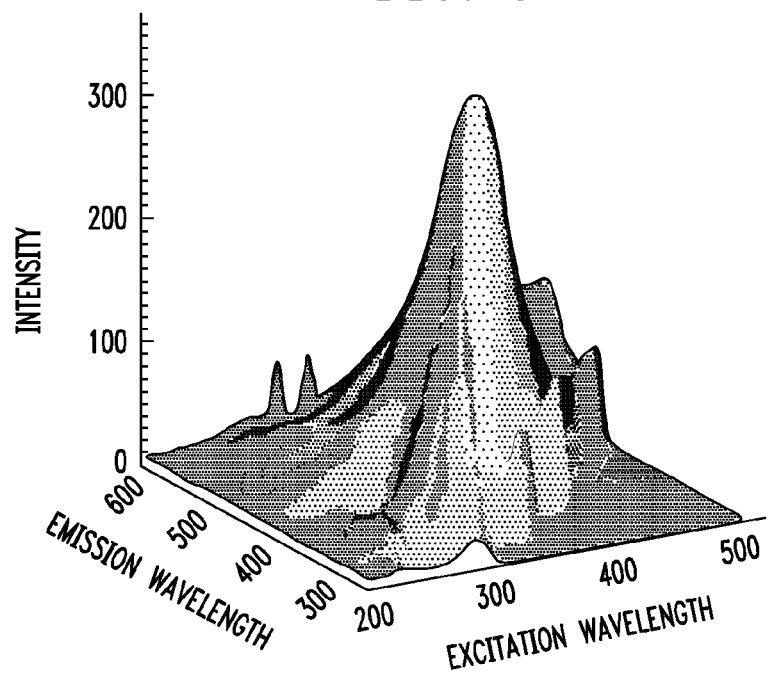
FIG. 5 depicts the total fluorescence spectrum of pseudomonas denitrificans, showing intensity as a function of emission wavelength and excitation wavelength.

As an example of the benefit of using multiple emission wavelengths to interrogate biological agents, consider *Pseudomonas Denitrificans*, which is a nitrate-reducing bacteria. The total fluorescence spectrum of *Pseudomonas Denitrificans* is depicted in FIGS. 4 and 5. As depicted in these Figures, *Pseudomonas Denitrificans* exhibits peaks in fluorescence emissions at about 340 nanometers and 440 nanometers. The peak at 340 nanometers corresponds to the presence of tryptophan and the peak at 440 nanometers corresponds to the presence of NADH. The tryptophan peak occurs at an excitation wavelength of about 290 nanometers and the NADH peak occurs at an excitation wavelength of about 360 nanometers. To the extent that sensing system 100 possesses an ability to expose a sample of *Pseudomonas Denitrificans* to excitation light at both 290 nanometers and 360 nanometers, rather than one or the other of these wavelengths, a more complete picture of the bacteria's fluorescence spectra is obtained. This, of course, increases the likelihood of accurate identification.

Figure 7:
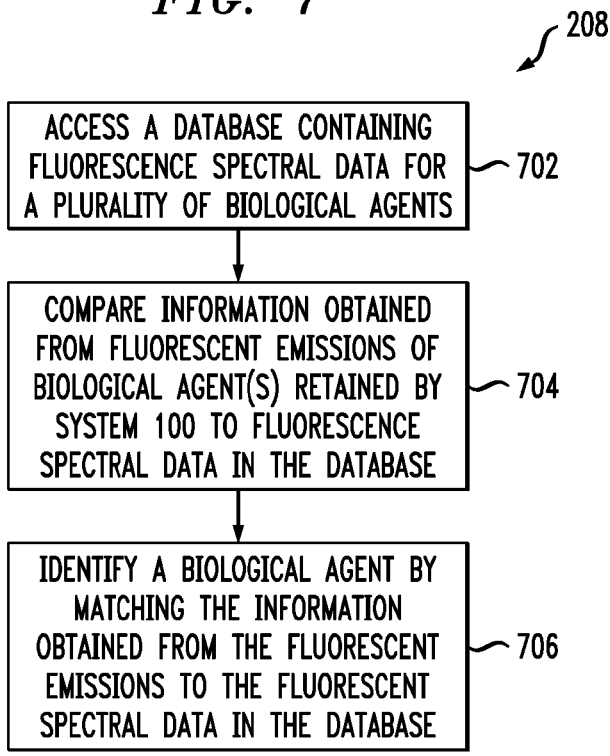
FIG. 7 depicts sub-operations of operation 208 of method 200.

The identification process is presented as a group of sub-operations of operation 208 in FIG. 7. In the illustrative embodiment, these sub-operations include:
  accessing a database of fluorescence spectral data for a variety of biological agents (sub-operation 702);

comparing information obtained from fluorescent emissions of unknown, possibly biological agents retained by sensing system 100 to fluorescence emission data in the database (sub-operation 704); and identifying a biological agent by matching the information obtained from the fluorescent emissions to the fluorescence emission data contained in the data base (sub-operation 706).

Figure 6:
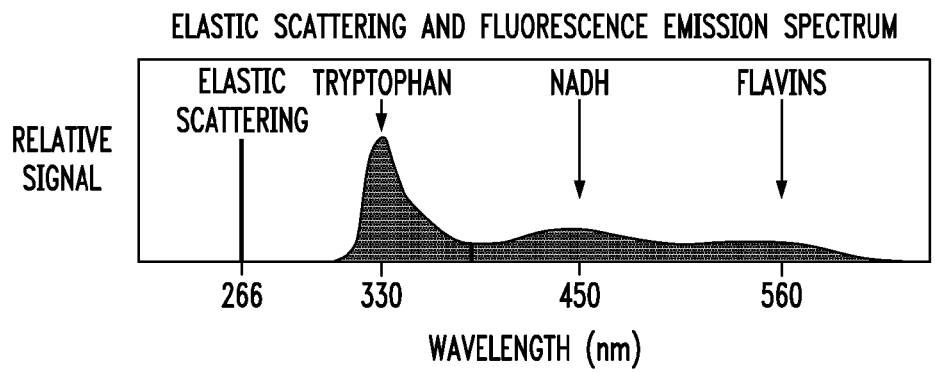
FIG. 6 depicts the fluorescent emission spectrum of pseudomonas at a particular excitation wavelength.

In some embodiments, the fluorescence emission data comprises peak emission wavelength(s), relative signal strength or intensity, and the corresponding excitation wavelength for a plurality of biological agents. In some other embodiments, the fluorescence emission data includes the complete emission spectra for a plurality of biological agents at certain excitation wavelengths. (FIG. 6 depicts the fluorescence emission spectra of Pseudomonas Denitrificans at an excitation wavelength of about 270 nanometers.) For the purposes of this Description and the appended Claims, the phrase "fluorescence emission data" means either of the above groups of characterizing information, or other collections of characterizing information, as appropriate for providing a "fingerprint" of a biological agent using information obtained from analysis of fluorescence emissions. In any case, the fluorescence emission data is organized into a database in known fashion.

The results of signal processing are presented via a graphical user interface. In some embodiments, the results are displayed as an "intensity" or "particle count" as a function of frequency or wavelength of the fluorescent emissions. In some embodiments, an alarm limit is displayed for each "type" (i.e., each different frequency or wavelength) of biological agent. If an alarm limit is exceeded, an alert (e.g., sound, flashing light, etc.) is provided. See, e.g., applicants' co-pending U.S. patent application Ser. No. 10/891,644.

It is to be understood that the above-described embodiments are merely illustrative of the present invention and that many variations of the above-described embodiments can be devised by those skilled in the art without departing from the scope of the invention. For example, in this Specification, numerous specific details are provided in order provide a thorough description and understanding of the illustrative embodiments of the present invention. Those skilled in the art will recognize, however, that the invention can be practiced without one or more of those details, or with other methods, materials, components, etc. In particular, as appropriate, features that are disclosed in co-pending U.S. patent application Ser. Nos. 10/891,644, 10/891,805 10/891,812 and 10/891,638 can be used in conjunction with the illustrative embodiment that is depicted and described herein. Those skilled in the art will know how to integrate such features into the illustrative embodiment of the present invention.

Furthermore, in some instances, well-known structures, materials, or operations are not shown or described in detail to avoid obscuring aspects of the illustrative embodiments. It is understood that the various embodiments shown in the Figures are illustrative, and are not necessarily drawn to scale. Reference throughout the specification to "one embodiment" or "an embodiment" or "some embodiments" means that a particular feature, structure, material, or characteristic described in connection with the embodiment(s) is included in at least one embodiment of the present invention, but not necessarily all embodiments. Consequently, the appearances of the phrase "in one embodiment," "in an embodiment," or "in some embodiments" in various places throughout the Specification are not necessarily all referring to the same embodiment. Furthermore, the particular features, structures, materials, or characteristics can be combined in any suitable manner in one or more embodiments. It is therefore intended that such variations be included within the scope of the following claims and their equivalents.

We claim:

1. An apparatus comprising:
   a stationary phase collection media for collecting a sample;
   a first plurality of light-emitting diodes (LEDs) for intermittently exposing said sample to electromagnetic radiation having a first peak wavelength;
   a second plurality of light-emitting diodes LEDs for intermittently exposing said sample to electromagnetic radiation having a second peak wavelength that is different than said first peak wavelength;
   circuitry for controlling operation of said first plurality of LEDs and said second plurality of LEDs to provide the intermittent exposure; and
   a plurality of photodetectors for detecting fluorescent emissions from said sample resulting from the exposure to electromagnetic radiation.

2. The apparatus of claim 1 wherein said first plurality of LEDs emit radiation at a peak wavelength that is less than 300 nanometers.

3. The apparatus of claim 1 wherein said second plurality of LEDs emit radiation at a peak wavelength that is greater than 300 nanometers.

4. The apparatus of claim 2 wherein said second plurality of LEDs emit radiation at a peak wavelength that is greater than 300 nanometers.

5. The apparatus of claim 2 wherein said second plurality of LEDs emit radiation at a peak wavelength that is greater than 350 nanometers.

6. The apparatus of claim 2 wherein said second plurality of LEDs emit radiation at a peak wavelength that is greater than 400 nanometers.

7. The apparatus of claim 1 wherein said first plurality of LEDs emit radiation at a peak wavelength that is less than 350 nanometers.

8. The apparatus of claim 7 wherein said second plurality of LEDs emit radiation at a peak wavelength that is greater than 380 nanometers.

9. The apparatus of claim 7 wherein said first plurality of LEDs emit radiation having a peak wavelength that is less than 400 nanometers and wherein said second plurality of LEDs emit radiation having a peak wavelength this is greater than 400 nanometers.

10. The apparatus of claim 1 wherein:
    said first plurality of LEDs emit radiation having a peak wavelength that is 300 nanometers or less;
    said second plurality of LEDs emit radiation having a peak wavelength that is greater than 300 nanometers and less than 350 nanometers; and further comprising
    at least one LED that emits radiation having a peak wavelength of 350 nanometers or more.

11. The apparatus of claim 1 wherein said first plurality of LEDs illuminate said sample at a different time than said second plurality of LEDs.

12. A method comprising:
    obtaining a sample of air;
    passing said sample through collection media, wherein said collection media is capable of retaining at least some particulates that are contained in said sample;

intermittently exposing said collection media with electromagnetic radiation having a first peak wavelength, wherein the exposure occurs at a first time;

intermittently exposing said collection media with electromagnetic radiation having a second peak wavelength, wherein the exposure occurs at a second time, and wherein the second time is different from the first time; and monitoring said collection media for fluorescent emissions; and issuing an alert when, based on monitored fluorescent emissions, said biological agent is determined to be present in excess of an acceptable upper limit thereof.

13. The method of claim 12 wherein monitoring comprises determining signal strength of first fluorescent emissions from particulates retained in said collection media when exposed to electromagnetic radiation having said first peak wavelength.

14. The method of claim 12 wherein said alert is issued when a signal strength of said fluorescent emissions exceeds a first value.

15. The method of claim 13 wherein monitoring further comprises comparing the determined signal strength for said first fluorescent emissions to fluorescence emission data, for each of a plurality of biological agents, which is contained in a database.

16. The method of claim 12 wherein monitoring comprises determining signal strength of second fluorescent emissions from particulates retained in said collection media when exposed to electromagnetic radiation having said second peak wavelength.

17. The method of claim 13 wherein monitoring comprises:

determining a signal strength of second fluorescent emissions from particulates retained in said collection media when exposed to electromagnetic radiation having said second peak wavelength; and comparing the determined signal strength of said second fluorescent emissions to said fluorescence emission data.

18. The method of claim 15 comprising determining an identity of a biological agent in the retained particulates by matching said signal strength for said first fluorescent emissions to fluorescence emission data in said database.

19. The method of claim 17 comprising determining an identity of a biological agent in the retained particulates by matching said signal strengths for said first fluorescent emissions and said signal strengths for said second fluorescent emissions to said fluorescence emission data in said database.

* * * * *